United States Patent [19]

Uthemann

[11] Patent Number: 5,213,963
[45] Date of Patent: May 25, 1993

[54] PROCEDURE FOR FINDING AND IDENTIFYING RED CELL ANTIBODIES BY MEANS OF THE SOLID PHASE METHOD

[75] Inventor: Horst Uthemann, Frankfurt, Fed. Rep. of Germany

[73] Assignee: Biotest Aktiengesellschaft, Frankfurt, Fed. Rep. of Germany

[21] Appl. No.: 885,064

[22] Filed: May 15, 1992

Related U.S. Application Data

[63] Continuation of Ser. No. 07/413,515, Sep. 27, 1989.

[30] Foreign Application Priority Data

Oct. 12, 1988 [EP] European Pat. Off. ............ 88116911

[51] Int. Cl.$^5$ .................. G01N 33/53; G01N 33/555; G01N 33/567
[52] U.S. Cl. ...................................... 435/7.25; 424/11; 436/513; 436/531; 436/821; 436/828
[58] Field of Search ................ 435/7.25, 11; 436/513, 436/520, 531, 821, 828

[56] References Cited

U.S. PATENT DOCUMENTS

| | | | |
|---|---|---|---|
| 4,328,183 | 5/1982 | Rosenfield et al. | 435/7.25 |
| 4,560,647 | 12/1985 | Stocker | 435/5 |
| 4,757,002 | 7/1988 | Joo | 435/7.92 |

FOREIGN PATENT DOCUMENTS

| | | |
|---|---|---|
| 0011669 | 1/1981 | European Pat. Off. . |
| 0058780 | 9/1982 | European Pat. Off. . |
| 0084102 | 7/1983 | European Pat. Off. . |
| 0223978 | 6/1987 | European Pat. Off. . |
| 8501354 | 3/1985 | PCT Int'l Appl. . |
| 8605591 | 9/1986 | PCT Int'l Appl. . |
| 2117514 | 10/1983 | United Kingdom . |

OTHER PUBLICATIONS

Transfusion 1990, 30, pp. 114-116, "Solid-phase antiglobulin test for screening and identification of red cell antibodies".
Beck et al., Med. Lab. Sci. 41:374-381, 1984.
Harlow et al., Antibodies: a Laboratory Manual, Cold Spring Laboratory, Cold Spring Harbor, NY, 1988, pp. 23-33.

*Primary Examiner*—Esther L. Kepplinger
*Assistant Examiner*—Donna C. Wortman
*Attorney, Agent, or Firm*—Sprung Horn Kramer & Woods

[57] ABSTRACT

A procedure for finding and identifying red cell antibodies by means of the solid-phase method, comprising contacting erythrocytes having selected antigen patterns with sera or plasmas that are to be tested for antibodies and transferred along with a polyspecific antihuman globulin reagent onto a substrate coated with protein A or protein G, thereby to transfer the detection or identification cells or, in the case of autocontrols, inherent cells.

3 Claims, No Drawings

PROCEDURE FOR FINDING AND IDENTIFYING RED CELL ANTIBODIES BY MEANS OF THE SOLID PHASE METHOD

This application is a continuation of application Ser. No. 413,515 filed Sept. 27, 1989, pending.

The invention concerns a procedure for finding and identifying red cell antibodies and a substrate and kit for carrying out the procedure.

The agglutination reaction has, due to its simplicity and wide range of application, become one of the most common methods of determining blood groups in recent decades. One essential drawback, however, is that it lacks an objective point of termination that can be readily determined automatically or visually in that the reactions that occur within the dilution series vary in intensity to the extent that weak reactions can be incorrectly interpreted as negative for example.

Solid-phase methods of finding and identifying erythrocytary antibodies and for cross-sampling have recently been suggested as an alternative to the agglutination reaction.

According to Plapp et al., A solid phase antibody screen, Am J Clin Pathol 82 (1984), 719; Beck et al, Semiautomated solid phase adherence assays for pretransfusion testing, Med Lab Sci 41 (1984), 374; and Capture-R solid phase assay system, Immunocor, 1987, the reactive solid-phase layer for example consists of erythrocytes with selected antigen patterns immobilized on the walls of the wells in polystyrene microtitration plates. Specific antibodies from sera or plasmas can be attached to these erythrocytes. This coating of the cells with antibodies can be made visible with what are called indicator cells (IgG-coated erythrocytes) by uniting the indicator cells to the coated and immobilized erythrocytes by way of antihuman globulin (polyspecific or monospecific anti-human IgG). The result is creation of a double layer of erythrocytes on the walls of the wells when there are enough red cell antibodies in the samples being tested. Negative results are evident from buttons of unattached indicator cells on the bottom of the well.

Beck et al and Rachel et al, A solid phase antiglobulin test, Transfusion 25 (1985), 24 describes a solid-phase method of cross-sampling that employs microtitration plates with wells coated with human IgG. The erythrocytes are preliminarily incubated with sera or plasmas that can contain antibodies against erythrocytes, and the coated or uncoated erythrocytes are washed and transferred along with an anti-human reagent to the IgG-coated microtitration plate. Erythrocytes coated with antibodies of the IgG type are attached by way of the anti-human IgG constituent of the reagent to the solid phase in the form of a visible film. Here as well, uncoated erythrocytes form buttons of sedimented cells.

Common to these methods is that positive reaction patterns appear as a coating of specifically attached erythrocytes on specially prepared solid phases, whereas negative reactions do not lead to the formation of a solid-phase coating. The various reaction patterns can be read visually or spectrophotometrically to arrive at an objective "yes" or "no."

The drawback of the solid-phase methods described up to now (IgG-coated indicator cells and IgG-coated wells), however, is that only red cell antibodies of the IgG type can be demonstrated, severely limiting the range of application of these methods.

The object of the invention is to provide a procedure for finding and identifying red cell antibodies within the scope of the solid-phase method as well as means of carrying out the procedure whereby not only red cell antibodies of the IgG type can be found and IgG-coated erythrocytes detected, but IgM and IgA antibodies can be found and complement-coated erythrocytes can be detected.

This object is attained by a process comprising contacting erythrocytes with selected antigen patterns with the sera or plasmas that are to be tested for antibodies and transferred along with an anti-human globulin reagent onto a coated substrate. In accordance with the invention, polyspecific anti-human globulin is employed to transfer the detection or identification cells or, in the case of autocontrols, the inherent (autologous) cells and in the substrate is coated with protein A or protein G.

Considering the large number of failed attempts that were carried out to find an obvious way of attaining the object, it was novel and surprising to discover that practically all the constituents of the polyspecific anti-human globulin employed could be attached by means of a protein-A or protein-G coating on a substrate, making polyspecific anti-human globulin attractive to use in the solid-phase method for the first time.

As will be illustrated by examples hereinafter, the procedure in accordance with the invention can be employed to detect a series of antibodies that cannot be detected by the known methods already described herein.

Thus, for example, the following antibodies are not detected by the known test systems:

1: e.g. anti-Le$^1$, anti-Le$^b$, anti-Le$^{a+b}$, and anti-Kn$^a$ of the IgM type (Table 2),
2: e.g. anti-Le$^a$, anti-Le$^b$, anti-Le$^{a+b}$, and anti-Kn$^a$ of the IgM type (Table 4),
3: e.g. anti-Kell of the IgM type (Table 2),
4: e.g. anti-Le$^a$ and anti-Le$^b$ of the IgM type (Table 1), and
5, the symposium, Rolih et al, Solid Phase Adherence Assays: Alternatives to Conventional Blood Bank Tests, Lab Med 16 (1985), 766: e.g anti-Le$^a$ and anti-Le$^b$ of the IgM type (Table III).

The substrates employed in the following tests were polystyrene microtitration plates, although any other type of substrate or substrate material known in conjunction with the solid-phase methods can be used. The protein-A or protein-G coatings on the substrates can be prepared for example by dissolving the protein in an isotonic sodium chloride solution or an appropriate buffer solution and bringing it into contact with the surface of an appropriate substrate. The concentration of the protein in the coating solution can range from 0.1 to 20 μg/ml. When the substrate is a microtitration plate, approximately 10 to 100 μl of coating solution per well has been proven practical. After standing for approximately 14 to 20 hours, the coating solution should be suctioned off and the wells washed 2 to 5 times with distilled water, optionally with a preservative added to it. The accordingly coated substrate is either used immediately or dried and appropriately stored.

The erythrocytes, optionally coated with antibodies and resuspended in polyspecific anti-human globulin, must only be added to these ready-to-use substrates, the microtitration plates for example, to carry out the test.

The invention will now be described in detail with reference to examples.

EXAMPLE 1

Coating with a substrate with protein

An essentially salt-free and powdered protein A that had been purified of cell walls and lyophilized was dissolved in an isotonic sodium chloride solution. The concentration of the coating solution was 0.5 μg/ml. Every well of a microtitration plate received 100 μl of this coating solution. After standing for 16 hours in a coating cabinet, the solution was suctioned off and the wells washed 3 times with distilled water containing a preservative. The coated plates were dried and welded into aluminum pouches.

EXAMPLE 2

Testing 1.0% suspensions of detection, identification, or patient-donor (autocontrol) erythrocytes were prepared in LISS. (low ionic strength solution) 100 μl of patient-donor sera or plasmas and 100 μl of the erythrocyte suspension were added to each well of a microtitration plate. The plates were covered and shaken and incubated in a culture box for 30 minutes at 37° C. The plates were then centrifuged for 2 minutes at 600 G.

The cells were washed 5 to 7 times with Coombs solution to remove unattached antibodies, and the salt solution was decanted off. The erythrocytes were resuspended by adding with a multichannel pipette 100 μl of a polyspecific anti-human globulin composed of

| | |
|---|---|
| anti-IgG, titer | 1:256 |
| anti-IgM, | 1:16 |
| anti-IgA, | 1:16 |
| anti-$C_3$b, | 1:32 |
| anti-$C_3$d, | 1:32 |
| Tween 20, 0.1%. | |

100 μl of the resuspended cells were added with a multichannel pipette to every well in the microtitration plates prepared as described in Example 1. The accordingly treated plates were allowed to stand 45 minutes at room temperature before being read.

EXAMPLE 3

Sensitivity of the test in accordance with the invention

To compare the sensitivity of the test procedure in accordance with the invention with that of a conventional antiglobulin test, the terminating points of series-diluted antibodies of known specificities were determined parallel in AB serum. The terminating points of the tests were interpreted as the highest dilutions that exhibited definitely visible reactions. When a panel of 3 search cells and 8 identification cells of a known antigen composition were tested, only the antibodies that reacted with all antigen-positive cells were considered identified. As will be evident from Table 1, the test procedure in accordance with the invention was usually 2 to 4 times more sensitive and evaluation of the strength of the reaction yielded essentially higher values.

TABLE 1

| | Sensitivities | | | |
|---|---|---|---|---|
| | Conventional method | | Invention: solid-phase method | |
| Antibody specificity | Titer | Evaluation | Titer | Evaluation |
| Rh system | | | | |
| D | 1024 | 42 | 8192 | 151 |
| C | 64 | 14 | 1024 | 77 |
| $c_w$ | 512 | 36 | 2048 | 96 |
| c | 64 | 27 | 1024 | 66 |
| C + D | 8192 | 83 | 128000 | 242 |
| E | 256 | 8 | 2048 | 55 |
| e | 2 | 22 | 16 | 125 |
| Kell system | | | | |
| K | 2048 | 26 | 4096 | 50 |
| $k_b$ | 32 | 39 | 64 | 120 |
| $K_p$ | 256 | 72 | 1024 | 201 |
| Kidd system | | | | |
| $Jk^a$ | 8 | 49 | 32 | 82 |
| $Jk^b$ | 8 | 13 | 16 | 44 |
| Duffy system | | | | |
| $Fy^a$ | 16 | 67 | 128 | 142 |
| $Fy^b$ | 4 | 19 | 16 | 94 |
| MNSs system | | | | |
| M | 256 | 168 | 256 | 216 |
| N | 16 | 111 | 16 | 120 |
| S | 1 | 13 | 16 | 100 |
| s | 8 | 37 | 16 | 88 |
| Lewis system | | | | |
| $Le^a$ | 256 | 64 | 1024 | 132 |
| $Le^b$ | 2 | 26 | 2 | 42 |
| Lutheran system | | | | |
| $Lu^a$ | 16 | 18 | 128 | 107 |
| $Lu^b$ | 16 | 50 | 16 | 89 |
| P system | | | | |
| $P_1$ | 4 | 29 | 8 | 64 |

EXAMPLE 4

Routine search and identification of donor antibodies

Antibody search and identification tests were carried out in parallel on 160 blood-donor sera and 1369 donor plasmas. Multiple antibodies were identified with various identification-cell panels. Table 2 presents the results.

TABLE 2

Results of routine donor-antibody search and identification

| | Number tested | Positive in test tube | % | Positive as tested with invention | % | Identification |
|---|---|---|---|---|---|---|
| Blood donor | 160 | 0 | 0 | 0 | 0 | |
| Plasma donor | 1369 | 8 | 0.58 | 8 | 0.58 | 3 anti-D |
| | | | | | | 1 anti-CD |
| | | | | | | 1 anti-CD, anti-$Yt^a$ |
| | | | | | | 1 anti-$C^w$ |
| | | | | | | 1 anti-e, anti-K, anti-$Fy^a$ |
| | | | | | | 1 anti-$Le^a$ |

EXAMPLE 5

Testing patient sera

The procedure in accordance with the invention was tested for three months with respect to its capacity to discover antibodies in patient sera in comparison with a conventional test-tube procedure for antibody search and identification. A total of 848 sera, including 68 umbilical-cord sera, were tested with autocontrols (n=491) and without autocontrols (n=357). Tables 3 and 4 show all the results.

TABLE 3

| Test tube | Inven- tion | Antibodies in patient sera | | |
|---|---|---|---|---|
| | | N | % | Identification and interpretation |
| Neg. | Neg. | 811 | 95.64 | 1 anti-D |
| Pos. | Pos. | 14 | 1.65 | 2 anti-CD |
| | | | | 1 anti-Kell |
| | | | | 1 anti-Le$^a$, reactive only in NaCl, not reactive in indirect Coombs test (ICT) |
| | | | | 2 anti-Le$^a$, reactive only in ICT |
| | | | | 3 cold antibodies, not reactive in ICT |
| | | | | 4 incomplete warm antibodies from patients with autoimmune hemolytic anemia (AIHA) |
| Neg. | Pos. | 20 | 2.36 | 1 anti-C |
| | | | | 1 anti-Kell |
| | | | | 1 imcomplete warm antibody from a patient with AIHA |
| | | | | 1 cold antibody |
| | | | | 16 antibodies not precisely identified |
| Pos. | Neg. | 3 | 0.35 | 3 false-positive results, negative when retested |

TABLE 4

| Test tube | Inven- tion | Auto-antibodies in patient sera | | |
|---|---|---|---|---|
| | | N | % | Identification and interpretation |
| Pos. | Pos. | 7 | 1.43 | Directly AHG positive: 5 (AIHA) |
| | | | | Directly AHG negative: 2 |
| Neg. | Neg. | 11 | 2.43 | Directly AHG positive: 2 (1 only C$_3$d positive 1 IgD positive, AIHA) |
| | | | | Directly AHG negative: 9 (further study needed) |
| Pos. | Neg. | 3 | 0.61 | Directly AHG negative: 3 false positives |
| Total: | | 21 | 4.28 | |

It will be understood that the specification and examples are illustrative but not limited of the present invention and that other embodiments within the spirit and scope of the invention will suggest themselves to those skilled in the art.

What is claimed is:

1. A method of finding and identifying red cell antibodies by the solid-phase method, comprising
   a) coating a solid substrate with protein A;
   b) incubating erythrocytes having known antigen patterns with a serum sample under conditions sufficient to coat the erythrocytes with serum antibodies;
   c) incubating the coated erythrocytes from step (b), antihuman globulin reagent containing anti-IgG, anti-IgM, anti-IgA, anti-C$_3$b and anti-C$_3$d and the coated substrate formed in step (a); and
   d) detecting the adherence of said erythrocytes to said coated substrate as an indication of the presence of said red cell antibodies.

2. The method of claim 1, wherein the substrate of (a) is a microtitration plate.

3. The method of claim 1, wherein the substrate of (a) is made of polystyrene.

* * * * *